United States Patent [19]

Drent

[11] Patent Number: 4,562,284

[45] Date of Patent: Dec. 31, 1985

[54] PROCESS FOR THE PREPARATION OF CARBOXYLIC ACIDS

[75] Inventor: Eit Drent, Amsterdam, Netherlands

[73] Assignee: Shell Oil Company, Houston, Tex.

[21] Appl. No.: 583,477

[22] Filed: Feb. 24, 1984

[30] Foreign Application Priority Data

Mar. 2, 1983 [NL] Netherlands ............................. 8300763

[51] Int. Cl.[4] ........................ C07C 51/09; C01B 25/14
[52] U.S. Cl. ..................................... 562/406; 260/413;
502/154; 502/166; 502/170; 562/496; 562/497;
562/517
[58] Field of Search ............... 502/154, 161, 166, 169,
502/170; 562/406, 496, 497, 517, 522; 260/413 R

[56] References Cited

U.S. PATENT DOCUMENTS

| | | | |
|---|---|---|---|
| 3,689,533 | 9/1972 | Schultz | 502/154 X |
| 3,818,060 | 6/1974 | Forster et al. | 502/154 X |
| 4,094,056 | 3/1980 | Antoniades | 562/517 |
| 4,190,729 | 2/1980 | Forster | 560/232 X |
| 4,273,936 | 6/1981 | Fiato et al. | 562/522 X |
| 4,334,094 | 6/1982 | Knifton | 562/496 X |

FOREIGN PATENT DOCUMENTS

| | | |
|---|---|---|
| 0072055 | 2/1983 | European Pat. Off. . |
| 1138601 | 1/1969 | United Kingdom ................ 502/154 |
| 1286224 | 8/1972 | United Kingdom . |

*Primary Examiner*—Natalie Trousof
*Assistant Examiner*—John T. Sullivan
*Attorney, Agent, or Firm*—Ronald R. Reper

[57] ABSTRACT

A process is disclosed for preparation of a carboxylic acid RCOOH wherein R represents certain alkyl, cycloalkyl or aralkyl groups, by heating a formic acid ester HCOOR in the presence of carbon monoxide, a soluble rhodium catalyst and an iodide or bromide source, promoted by certain oxygen-containing compounds of phosphorus, arsenic or antimony.

6 Claims, No Drawings

PROCESS FOR THE PREPARATION OF CARBOXYLIC ACIDS

BACKGROUND OF THE INVENTION

The invention relates to a process for the preparation of a carboxylic acid RCOOH wherein R represents an alkyl, cycloalkyl or aralkyl group, by heating an ester of formic acid HCOOR in the presence of carbon monoxide, a soluble rhodium catalyst and an iodide and/or bromide source. The invention relates in particular to the preparation of acetic acid from methyl formate.

U.K. Pat. Specification No. 1,286,224 and U.S. Pat. No. 4,194,056 describe processes for the preparation of acetic acid wherein methyl formate is heated in the presence of carbon monoxide, a rhodium catalyst and a halogen-containing promoter, particularly methyl iodide. However, rhodium is costly and investigations have been carried out to find processes in which practicable results are obtained by using less expensive catalysts under moderate reaction conditions. Such a process, in which, among other things, a palladium or ruthenium compound is used, is disclosed in German Offenlegungsschrift No. 3,046,899. However, the conversion of methyl formate proceeds at a considerably lower rate than in the presence of rhodium compounds, which is the reason why, generally, the use of the latter compounds remains preferred. On account of the high cost of rhodium, however, it is important that the catalyst system which eventually is formed by interaction of the rhodium compound with carbon monoxide, halogen-containing promoter and other ligands in the reaction mixture, be as active as possible, so that under moderate reaction conditions the reaction will proceed at a rate suitable for use in actual practice.

The rate at which the carboxylic acid is formed can be expressed as the number of gram atoms carboxylic acid that are formed per gram rhodium per gram halogen present in the halogen-containing promoter per hour. This is an adequate method of expression when determining the activity of the catalyst system, since generally the reaction rate is directly proportional to both the quantity of rhodium and the quantity of halogen-containing promoter present in the reaction mixture. Not only is it important for the quantity of carboxylic acid formed per gram rhodium per hour to be as large as possible, but also for this to be achieved in the presence of as little halogen-containing promoter as possible. Not only do halogen compounds, such as for instance methyl iodide, often have corrosive properties, they are also fairly volatile, so that during recovery of the reaction product by distillation they leave the reactor and must be recirculated. For a process to be carried out on a large scale it is naturally of importance that the quantity of material to be recirculated is kept as small as possible.

It has now surprisingly been found that certain compounds of pentavalent phosphorus, arsenic or antimony, which will be defined hereinafter, have a strong promoter activity during the preparation of acetic acid from methyl formate in the presence of a rhodium catalyst and an iodide and/or bromide source.

SUMMARY OF THE INVENTION

The invention therefore relates to a process for the preparation of a carboxylic acid RCOOH wherein R represents and alkyl, cycloalkyl or aralkyl group, by heating an ester of formic acid HCOOR in the presence of carbon monoxide, a soluble rhodium catalyst and an iodide and/or bromide source, and as promoter at least one compound having the formula

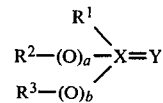

wherein X represents phosphorus, arsenic or antimony and Y oxygen, sulphur or selenium and $R^1$ represents hydrogen or an unsubstituted or substituted hydrocarbon group, and either a or b, independently are 0 or 1 and $R^2$ and $R^3$ each represents an unsubstituted or substituted hydrocarbon group or a and b are both 0 and $R^2$ and $R^3$ together with X form a heterocyclic group, or a complex of a compound of formula I with a hydrocarbon iodide or bromide, an acyl iodide or bromide or a hydrogen iodide or bromide.

DESCRIPTION OF PREFERRED EMBODIMENTS

With the aid of the process according to the invention an ester of formic acid can be converted into a carboxylic acid at a formation rate, which expressed as g carboxylic acid per g rhodium per g iodine or bromine per hour, is considerably higher than the formation rate achieved using the process according to U.K. Pat. Specification No. 1,286,224 and U.S. Pat. No. 4,194,056. In Example 1 of the British patent specification mentioned methyl formate in the presence of $Rh(CO)Cl[(C_6H_5)_3P]_2$, methyl iodide and carbon monoxide at a temperature of 200° C. yields 122 g acetic acid/g Rh/g I/hour. Considering the fact that a decrease in temperature of 10° C. causes the reaction rate to become almost twice as low, the formation rate of acetic acid will be about 15 g acetic acid/g Rh/g I/hour at 170° C. By means of the process of the invention the much higher rate, at 170° C., of 85 g acetic acid/g Rh/g I/hour can easily be obtained.

In U.S. Pat. No. 4,194,056 in Example 1 the conversion of methyl formate is carried out in a microreactor at 170° C. and in the presence of $RhCl[(C_6H_5)_3P]_3$, methyl iodide and carbon monoxide. From the data mentioned there can be computed a formation rate of 143 g acetic acid/g Rh/g I/hour. From Example 2 it can be further deduced that at 170° C. and a low degree of conversion the formation rate is 292 g acetic acid/g Rh/g I/hour and from Example 7 a formation rate can be computed at 200° C. of 1100 g acetic acid/g Rh/g I/hour, which amounts to a formation rate at 170° C. of about 137 g acetic acid/g Rh/g I/hour. However, in a repeat of Example 2 on a larger scale, in a 300 ml autoclave, the formation rate of the acetic acid was no more than 53 g acetic acid/g Rh/g I/hour, and thus considerably lower than that achieved with the process according to the invention. Possibly the difference between the latter formation rate and the formation rate that can be computed from the experimental results mentioned in U.S. Pat. No. 4,194,056 can be accounted for by inaccurate measuring of the temperature prevailing in the microreactor. In the experimental part of the present application it will be demonstrated that even in the presence of the catalyst $RhCl[(C_6H_5)_3P]_3$ which is used by preference in U.S. Pat. No. 4,194,056 do the compounds of general formula I to be used according to the invention have promoter activity, and that therefore the process according to the invention constitutes an improvement over the process according to the U.S. patent.

The triphenylphosphine present in the catalyst used in U.K. Patent Specification No. 1,286,224 and U.S. Pat. No. 4,194,056 has the drawback that under the reaction conditions used it may produce decomposition products which will contaminate the reaction mixture and, particularly, the catalyst, which is a disadvantage especially when the process is operated continuously. The compounds of pentavalent phosphorus, arsenic or antimony which according to the invention are used as promoters are stable under the reaction conditions and cause no contamination of the reaction mixture and/or the catalyst.

The alkyl group which may be present in the ester of formic acid HCOOR, preferably contains 1-20, in particular 1-6, carbon atoms, the cycloalkyl group preferably contains 3-10, in particular 5 or 6 carbon atoms and the aralkyl group 7-15, in particular 7-10, carbon atoms. The process according to the invention may be used for instance for preparing propionic acid, butyric acid, lauric acid, cyclohexanecarboxylic acid, phenylacetic acid and in particular acetic acid.

The soluble rhodium compound may be an oxide or hydroxide or an inorganic or organic salt, or a complex compound containing one or more ligands, such as carbon monoxide, amines, phosphines, arsines, stibines or an olefinically unsaturated compound. Examples of suitable rhodium compounds are $RhCl_3$, $RhBr_3$, $RhI_3$, $Rh(NO_3)_3$, $Rh_2(SO_4)_3$, rhodium triformate, rhodium triacetate, rhodium trinaphthenate, dirhodium octacarbonyl, tetrarhodium dodecacarbonyl, hexarhodium hexadecacarbonyl, rhodium dicarbonylacetylacetonate, $Rh(C_5H_5N)_3Cl_3$, $RhCl[(C_6H_5)_3P]_3$, $RhBr[(C_6H_5)_3P]_3$, $RhCl[(C_6H_5)_3P]_3H_2$, $Rh(CO)Cl[(C_6H_5)_3P]_2$, $Rh(CO)_4I_2$ and $Rh(CO)[(C_6H_5)_3As]_2$. A very suitable rhodium compound is $RhCl_3.3H_2O$.

The quantity of rhodium compound preferably lies between $3.10^{-6}$ and $10^{-2}$, in particular between $10^{-5}$ and $10^{-2}$ and most preferably between $3.10^{-5}$ and $3.10^{-3}$, gram atom rhodium per mol ester of formic acid.

The iodide and/or bromide source may be for instance elemental iodine and bromine, or hydrogen iodide or hydrogen bromide or a compound $R^4I$, $R^4Br$, $R^4COI$ or $R^4COBr$, where $R^4$ represents an alkyl group optionally substituted with bromine or iodine, or an aralkyl group preferably having not more than 12 carbon atoms. Compounds $R^4I$ and $R^4COI$, wherein $R^4$ represents an alkyl group having 1-4 carbon atoms in particular methyl iodide, are especially preferred iodine sources. Specific examples of other suitable iodide and/or bromide sources are $CH_3Br$, $C_2H_5I$, $C_4H_9I$, $C_8H_{17}I$, $CH_2I_2$, $C_2H_4I_2$, $CH_2IBr$, $CHI_3$ and $C_2H_4IBr$. Ammonium, phosphonium, arsonium and stibonium iodides and bromides may also be used as iodide and/or bromide sources. Examples of such compounds are triphenylphosphonium iodide, methyltriphenylphosphonium iodide, tetramethylammonium iodide, tetraisopropylammonium iodide, tetrabutylammonium bromide and tetrabutylammonium iodide. If the catalyst contains an iodide or bromine compound or rhodium, said compound may also act as iodide or bromide source.

The quantity of iodide and/or bromide source, viz, the total number of gram atoms I and/or Br present in the reaction mixture, generally lies between 1 and 1000, preferably between 3 and 500 and in particular between 10 and 300, gram atoms I and/or Br per gram atom rhodium.

The hydrocarbon groups $R^1$, $R^2$ and $R^3$ which may be present in the compound of formula I to be used as promoter in the process according to the invention may be alkyl, cycloalkyl, aryl, aralkyl or alkaryl groups which preferably have not more than 30, in particular not more than 20, carbon atoms and optionally are substituted with one or more substituents, such as for instance halogen atoms or a group $R^5R^6{}'X=Y$, wherein X and Y have the meanings given hereinbefore and $R^5$ and $R^6$ each represent an unsubstituted or substituted hydrocarbon group. If $R^2$ and $R^3$ together with X form a heterocyclic group, this group preferably contains not more than 20 carbon atoms. Specific examples are the phospholane, phosphorinane and phosphohepane groups, wherein the groups $R^2$ and $R^3$ together represent an alkylene group having 4, 5 or 6 carbon atoms, respectively, and the 9-phosphabicyclo[4.2.1]nonane group and the 9-phosphabicyclo[3.3.1]nonane group. These heterocyclic groups may for instance be substituted with hydrocarbon groups.

Compounds of formula I where a and b are both 0, X is phosphorus and Y oxygen or sulphur and $R^1$, $R^2$ and $R^3$ represent alkyl groups having 1-12 carbon atoms or cycloalkyl, aryl, aralkyl or alkaryl groups having 5-12 carbon atoms are preferred. Particularly preferred are compounds of general formula I wherein Y is oxygen and $R^1$, $R^2$ and $R^3$ represent alkyl groups having 1-12 carbon atoms and/or phenyl groups which may optionally be substituted with one or more methyl or ethyl groups.

Specific examples of compounds of formula I are the oxides, sulphides or selenides of secondary and tertiary phosphines, arsines and stibines such as trimethylphosphine oxide, diethylphosphine oxide, triethylphosphine oxide, tri-n-butylphosphine oxide, trioctylphosphine oxide, diphenylphosphine oxide, tri-p-tolylphosphine oxide, tricyclohexylphosphine oxide, diphenylethylphosphine oxide, tri(1-naphthyl)phosphine oxide, trimethylphosphine sulphide, tri-4-chlorophenylphosphine sulphide, triphenylphosphine sulphide, tricyclohexylphosphine sulfide, tri-n-butylphosphine sulphide, triphenylphosphine selenide, tris(1-naphthyl) phosphine selenide, triethylarsine oxide, triphenylstibine oxide and triphenylarsine sulphide. Triphenylphosphine oxide is a very suitable promoter. Specific examples of compounds having a heterocyclic phosphorus-containing group are 1-phenylphospholane oxide, 1-phenylphosphorinane oxide, 9-phenyl-9-phosphabicyclo[4.2.1]nonane oxide, 9-phenyl-9-phosphabicyclo[3.3.1]nonane oxide, 9-eicosyl-9-phosphabicyclo[4.2.1]nonane oxide, 9-eicosyl-9-phosphabicyclo[3.3.1]nonane oxide 1-phenylphospholane sulphide, 1-phenylphosphorinane sulphide.

Examples of compounds of the general formula I wherein a and/or b are 1, are the alkyl, cycloalkyl, aryl, aralkyl or alkaryl esters of phosphonic acis and phosphinic acids and the analogues of these compounds wherein the double-bonded oxygen atom has been replaced by a sulphur atom or a selenium atom and/or the phosphorus atom by an arsenic atom or an antimony atom. Specific examples of such compounds are dimethyl methylphosphonate, diphenyl methylphosphonate, diethyl methylphosphonate, methyl diethylphosphinate and phenyl dimethylphosphinate.

Specific examples of compounds of formula I, wherein one or more of the groups $R^1$, $R^2$ and $R^3$ have been substituted with a group $R^5R^{6'}X=Y$, are the compounds:

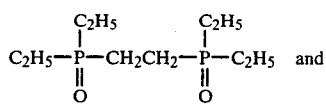 and

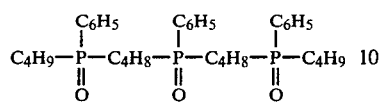

Finally, in the process according to the invention complexes obtained by reaction of a compound of formula I with a hydrocarbon iodide or bromide, such as $CH_3I$, and acyl iodide or bromide, or hydrogen iodide or bromide may be used. Examples of such complexes are: $[(C_6H_5)_3PO\text{-}H\text{-}OP(C_6H_5)_3]^+I_3^-$ and $[(C_2H_5)_3AsO\text{-}H\text{-}OAs(C_2H_5)_3]^+I^-$. It is likely that such complexes are also formed in situ by reaction of the compound of formula I with iodine or bromide compounds present in the reaction mixture.

If in the compound of formula I X represents phosphorus and Y oxygen, and a and b are 0, this compound can be produced in situ by using not the relevant compound of general formula I, but the corresponding phosphine and carrying out the reaction in the presence of molecular oxygen or hydrogen peroxide.

The quantity of compound of formula I used as promoter in the process according to the invention may vary within wide ranges, for instance between 0.1 and 300 mol per gram atom rhodium. Advantageously 1–200, particularly 10–150, mol per gram atom rhodium is used.

The process according to the invention is preferably carried out at a temperature between 110° and 225° C., particularly between 125° and 200° C. The reaction is generally carried out at a partial CO pressure between 0.5 and 70 bar. High pressures, for instance of up to 1000 bar, may be used if desired, but generally these are unattractive from the technical and economic point of view.

The carbon monoxide used in the process according to the invention may optionally be mixed with other gases, such as for instance carbon dioxide, hydrogen, methane, nitrogen or noble gases. Synthesis gas may be used as a carbon monoxide source.

The process is carried out in the liquid phase. Usually there is no need for the use of any (additional) solvent, since the ester of formic acid which is used as a starting material and/or the carboxylic acid formed will act sufficiently as solvent. Other components of the reaction mixture, for instance a liquid iodide source, such as for instance $CH_3I$, may act as solvents as well. Additional amounts of these compounds may be added to the reaction mixture, if desired. Suitable (additional) solvents are, for instance, acetic acid, propionic acid, methyl acetate, butyrolactone, acetic anhydride, methyl-t-butyl ether, diglyme, tetraglyme, tetrahydrofuran, 1,4-dioxane, 1,3-dioxane, dimethyl sulphone, diethyl sulphone, methyl ethyl sulphone, methyl butyl sulphone, sulpholane, 2-methyl sulpholane, 3-methyl sulpholane and 2-methyl-4-butyl sulpholane. The solvent may have promoter activity, i,e., it may have a favorable effect on the activity and/or the selectivity of the catalyst system. If desired, other promoters, such as for instance phosphines or metal compounds, for example compounds of other group VIII metals, may also be added to the reaction mixture. The process is preferably carried out under virtually anhydrous conditions. The presence of minor quantities of water such as may be found in commercially available starting materials, for example rhodium trichloride trihydrate, are permissible, however.

The process according to the invention can be carried out continuously, semi-continuously or batchwise. The reaction mixture obtained may be worked up with the aid of known techniques, such as fractional distillation. Further, the process may be integrated in existing processes for preparing the starting materials or for further processing the carboxylic acid obtained.

EXAMPLE 1

A magnet-driven Hastelloy C autoclave (Hastelloy is a trademark) having a capacity of 300 ml was charged with 0.25 mmol $RhCl_3.3H_2O$, 40 ml methyl formate and 10 ml acetic acid and the quantities given in Table A of methyl iodide and triphenylphosphine oxide or triphenylphosphine. The autoclave was flushed with carbon monoxide and filled with carbon monoxide at a pressure of 30 bar and subsequently heated for the periods of time given in Table A at the temperatures likewise given in the Table. After the reaction time the reaction mixture was cooled and the quantities of acetic acid, methyl formate and methyl acetate were determined by gas-liquid chromatography. From these quantities was computed the quantity of methyl formate converted into acetic acid. The reaction rate was expressed as the number of grams of acetic acid formed per gram rhodium per gram iodine per hour.

TABLE A

| Experiment No. | Methyl iodide, mmol | Triphenyl-phosphine oxide, mmol | Temperature °C. | Reaction time, h | Reaction rate, g, acetic acid/ g Rh/g I/h |
|---|---|---|---|---|---|
| 1* | 60 | — | 160 | 5 | 4.9 |
| 2* | 60 | 4 | 160 | 5 | 37.3 |
| 3 | 17 | 17 | 170 | 2.9 | 86.3 |
| 4 | 8.75 | 16 | 170 | 3 | 85 |
| 5 | 17 | 32 | 170 | 3 | 100 |
|  |  | Triphenyl-phosphine, mmol |  |  |  |
| 6 | 17 | 17 | 170 | 3 | 40.3 |

*CO contained $H_2$ ($P_H$ = 5 bar; $P_{CO}$ = 30 bar).

The table shows the strong promoter activity of triphenylphosphine oxide. Comparison of Experiment 3 with Experiment 6 teaches that the promoter activity of triphenylphosphine oxide is more than twice as strong as that of triphenylphosphine.

EXAMPLE 2

Example 2 of U.S. Pat. No. 4,194,056 was repeated but using quantities that were six times larger in a 300-ml Hastelloy C autoclave. The autoclave was charged with 36 g methyl formate, 1.344 g methyl iodide and 0.6 g tris(triphenylphosphine)chlororhodium (I) $(RhCl[(C_6H_5)_3P]_3)$. The autoclave was flushed with carbon monoxide, filled with carbon monoxide having a pressure of 30 bar and then heated to 170° C. After a reaction time of 4 hours the reaction mixture was cooled and analyzed by gas-liquid chromatography and the quantities of acetic acid, methyl acetate and methyl formate were determined. The formation rate of the acetic acid was found to be 53 g acetic acid/g Rh/g I/hour.

This experiment shows that the conversion rate achieved with the process according to the U.S. patent is lower than the conversion rate achieved with the process according to the invention.

Repetition of the experiment using in addition an amount of 8 mmol triphenylphosphine oxide in the reaction mixture gave a formation rate of 65 g acetic acid/g Rh/g I/hour, which shows that also in the presence of a triphenylphosphine-containing catalyst does triphenylphosphine oxide act as a promoter.

I claim:

1. A process for the preparation of a carboxylic acid RCOOH wherein R represents an alkyl group having 1-20 carbon atoms, a cycloalkyl group having 5-10 carbon atoms or an aralkyl aralkyl group having 7-13 carbon atoms by heating at a temperature from about 110° to about 225° C. an ester of formic acid HCOOR in the presence of carbon monoxide, and a catalyst system consisting essentially of a soluble rhodium catalyst and an iodide and/or bromide source, and as promoter a compound of the formula

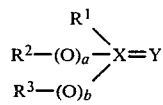

wherein a and b are both 0, X is phosphorus and Y is oxygen or sulphur and $R^1$, $R^2$ and $R^3$ each represent alkyl groups having 1-12 carbon atoms or cycloalkyl, aryl, aralkyl or aralkyl groups having 5-12 carbon atoms, or a complex of a compound of formula I with a hydrocarbon iodide or bromide, an acyl iodide or bromide or a hydrogen iodide or bromide.

2. A process as in claim 1, wherein R is an alkyl group having 1-6, a cycloalkyl group having 5 or 6, or an aralkyl group having 7-10 carbon atoms.

3. A process as in claim 1, wherein the iodide and/or bromide source is at least one of elemental iodine or bromine, hydrogen iodide, hydrogen bromide or a compound $R^4I$, $R^4Br$, $R^4COI$ or $R^4COBr$, wherein $R^4$ represents alkyl group optionally substituted with bromine or iodine, or an aralkyl group having not more than 12 carbon atoms.

4. A process as in claim 1, wherein the total number of gram atoms I and/or Br present in the reaction mixture is in the range from about 3 to about 500, gram atoms of I and/or Br per gram atom of rhodium.

5. A process as in claim 1, wherein Y is oxygen and $R^1$, $R^2$ and $R^3$ each represent a group selected from alkyl groups having 1-12 carbon atoms and/or phenyl groups which may optionally be substituted with one or more methyl or ethyl groups.

6. A process as in claim 1, wherein the reaction is carried out at a temperature between 125° and 200° C.

* * * * *